United States Patent [19]

Hahn

[11] Patent Number: 4,651,338
[45] Date of Patent: Mar. 17, 1987

[54] COOLING SYSTEM FOR A TOMOGRAPH APPARATUS

[75] Inventor: Günter Hahn, Nuremberg, Fed. Rep. of Germany

[73] Assignee: Siemens Aktiengesellschaft, Berlin and Munich, Fed. Rep. of Germany

[21] Appl. No.: 753,616

[22] Filed: Jul. 10, 1985

[30] Foreign Application Priority Data

Oct. 8, 1984 [DE] Fed. Rep. of Germany ....... 3436867

[51] Int. Cl.[4] .......................... H01J 35/10; H01J 35/12
[52] U.S. Cl. ...................................... 378/199; 378/200
[58] Field of Search .................. 378/4, 199, 200, 210; 343/763

[56] References Cited

U.S. PATENT DOCUMENTS

| | | | |
|---|---|---|---|
| 1,565,969 | 12/1925 | Spiro | 378/199 |
| 1,874,478 | 8/1932 | Fayer | 378/200 |
| 2,313,145 | 3/1943 | Heger | 378/200 |
| 4,115,697 | 9/1978 | Hounsfield et al. | 378/199 |
| 4,538,125 | 8/1985 | Beckmann et al. | 343/763 |

FOREIGN PATENT DOCUMENTS

| | | | |
|---|---|---|---|
| 0109204 | 5/1984 | European Pat. Off. | 378/4 |
| 2026812 | 2/1980 | United Kingdom | 378/200 |

*Primary Examiner*—Janice A. Howell

[57] ABSTRACT

A tomographic apparatus has a rotatable part mounted for rotation in a track of a stationary part. The apparatus has a radiation field generating element which requires cooling, and has a coolant circulator for that purpose. As a further part of the cooling system, the coolant is circulated around the exterior of the rotatable part in the vicinity of the track, and a number of cooling fins in heat-transferring communication with the coolant project into the track for dissipating heat from the coolant. An additional coolant may be circulated within the track for assisting in removal of heat from the cooling fins. The rotatable part may be further provided with a transmitting antenna, and the stationary part provided with a receiving antenna, for transmitting signals between those parts relating to examination of a subject.

6 Claims, 2 Drawing Figures

COOLING SYSTEM FOR A TOMOGRAPH APPARATUS

BACKGROUND OF THE INVENTION

1. Field of the Invention

The present invention relates to devices for examining a patient by generating an examination field enveloping the patient and detecting the interaction of the patient with the examination field, and in particular to a computer tomographic examination apparatus and a cooling system therefore.

2. Description of the Prior Art

Patient examining systems are known which generate an examining field, such as an x-ray field or a magnetic field, which examination field interacts with the patient, producing various sets of data which can be analyzed to provide an image of selected sections of the patient. Such field generating means and the detector means therefore generally create a significant amount of heat in the operation thereof, and such devices must therefore be provided with means for dissipating the generated heat.

For this purpose, conventional devices generally employ an oil circulation system wherein oil is utilized as the coolant and the oil is circulated around the components to be cooled. The oil is generally further circulated past a blower for dissipating heat from the oil. In devices having a rotatable part mounted for rotation in a track of a stationary part, the oil coolant is generally circulated within the rotation track, thereby resulting in considerable heating of the interior volume of the tomographic apparatus. This also presents the problem of localized areas of elevated temperature arising. The sensitive electronic measuring apparatus is disadvantageously influenced to a great extent by such localized heating.

SUMMARY OF THE INVENTION

It is an object of the present invention to provide a heat dissipating system for a patient examining apparatus, such as a computer tomograph, which permits heat to be dissipated from the rotation track to an exterior of the apparatus. The above object is inventively achieved in an apparatus wherein the stationary part has a channel in which the rotatable part is mounted for rotation with at least one inlet opening and at least one outlet opening for a cooling agent to be circulated within the track. The oil coolant, or any other suitable type of coolant, which is circulated around the heat-generating parts of the apparatus is circulated around the rotation track as well, and a plurality of cooling ribs are disposed to project into the track in heat-transferring communication with the heat-generating device coolant. The coolant which is circulated through the track by means of the inlet and outlet openings is in contact with the cooling fins so as to remove heat therefrom and prevent buildup of heat in the track. In the case of a computer tomograph, the cooling ribs or fins can be provided on the rotating track in a circular arrangement. The rotatable part may contain a channel near the periphery thereof through which the primary coolant, such as oil, is circulated, and the fins may project from the channel in heat-transferring contact therewith. Heat is thus eliminated from the components carried on the rotating part toward the exterior of the apparatus without the interior space of the apparatus becoming impermissibly heated.

The apparatus may further include a rotating signal transmitter disposed in the track for contact-free signal transmission from the detector in the rotating part to processing equipment and other devices located in or external to the stationary part. This transmitter may be formed by high frequency antennae respectively disposed on the rotating part and the stationary part for radio transmission of signals therebetween.

DESCRIPTION OF THE PREFERRED EMBODIMENTS

Figure 1:
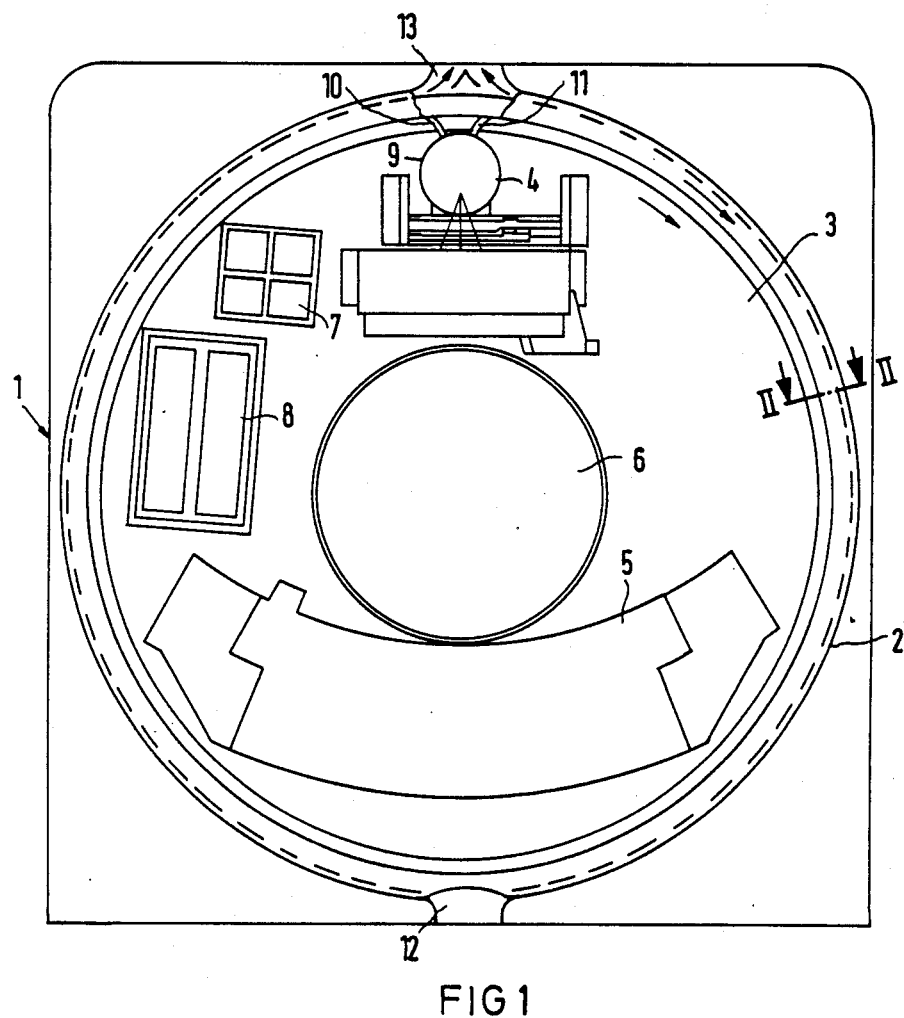
FIG. 1 is a schematic side view of a patient examining apparatus constructed in accordance with the principles of the present invention.

A computer tomograph generally referenced at 1 in FIG. 1 has a stationary part 2 and a rotatable part 3. The rotatable part 3 is mounted for rotation in a circular track in the stationary part 2. The rotatable part 3 carries a means for generating an examining field 4, such as an x-ray generator, and a detector 5 for detecting the interaction of a patient in a central opening 6 with the field generated by the generating means 4. For scanning an examination subject lying in the opening 6, the rotatable part 3, with the radiation 4 and the radiation detector 5, is rotated around the radiography subject so that the subject is irradiated from a number of directions. As is known, computer calculations are then undertaken from the received radiation intensity data so as to provide an image of a section of the examination subject based on the attenuation values thereof. The rotatable part 3 may also have a voltage supply 7 and supplementary electronic apparatus 8 thereon.

For cooling the components on the rotatable part 3, in particular the generator 4, oil is pumped through the generator housing 9. The oil is supplied to the housing 9 via an inlet conduit 10, and exits therefrom via an outlet conduit 11. The cooling oil flows through a conduit or channel disposed near the peripheral or exterior side of the rotatable part 3, and extending completely therearound. For this purpose, a circulating pump (not shown) is arranged on the rotatable part 3.

Removal of heat from the cooling oil is undertaken by means of cooling air which is supplied to the oil coolant by an inlet air connection or nozzle 12. The air exits through an air outlet connection or nozzle 13. Further details of such heat dissipation are explained in connection with FIG. 2, which is a section taken through the track in which the rotatable part is mounted.

Figure 2:
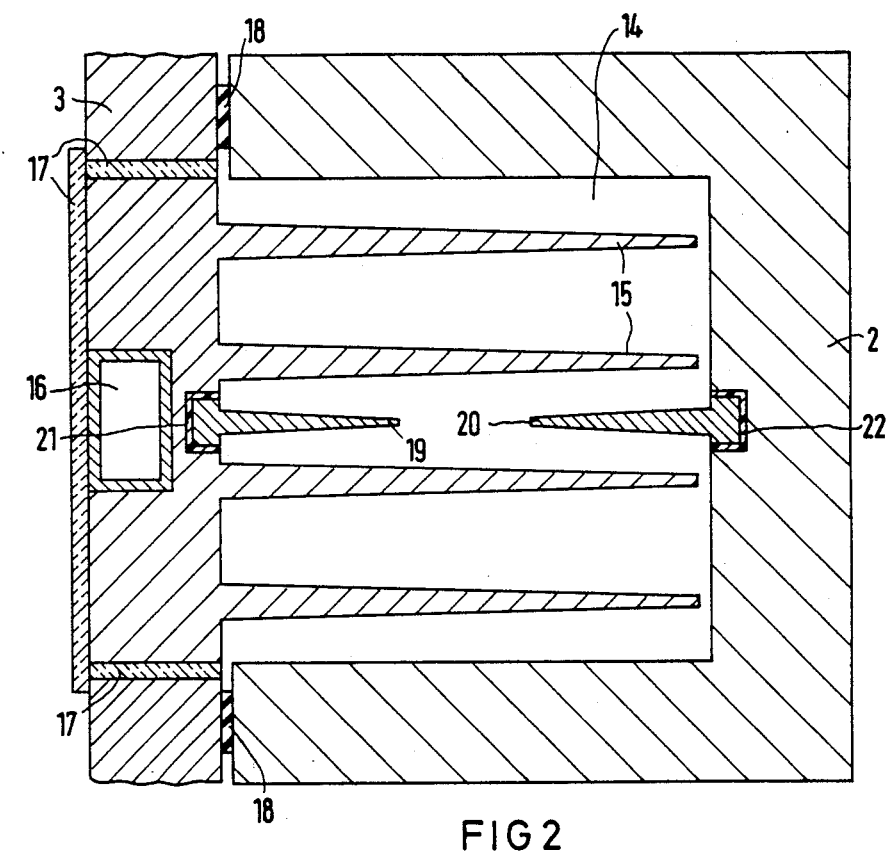
FIG. 2 is a sectional view taken along line II—II of FIG. 1 showing a portion of the cooling system for the apparatus constructed in accordance with the principles of the present invention.

As shown in FIG. 2, the stationary part 2 has a U-shaped ring channel 14 through which the aforementioned cooling air is conveyed by a ventilator from the air inlet connection 12 to the air outlet connection 13. A plurality of cooling ribs or fins 15 project into the channel 14 and are arranged in heat-transferring communication with the cooling oil circulating through the rotatable portion 3, such as by direct contact with the rotatable part 3. The rotatable part 3 has a conduit 16 through which the cooling oil is circulated. As the rotatable part 3 rotates, the cooling fins 15 in the channel 14 move with the rotatable part, and cooling air flow over and in contact with the fins 15, thereby greatly assisting in elimination of heat from the cooling oil in the channel 16 via the fins 15. Moreover, the heat which is dissipated is directed with the flow of cooling air to an external location, so that the interior of the apparatus does not become overheated. To further assist in prevention of overheating of the interior, heat insulation 17 is provided on three sides of the channel 16, insuring that substantially all of the heat from the channel 16 is transferred to the fins 15 rather than to other areas. A seal 18 is provided to prevent cooling air from flowing out of the channel 14 between the rotating part 3 and the stationary part 2.

Although not shown in the drawings, the detector 5 may also be cooled by circulating cooling oil around that component, and this cooling oil either being directed to the same conduit 16 for heat dissipation as described above, or to another conduit similarly disposed.

Signal transmitting means may also be provided within the channel 14 in the form of a rotating transmitter. The rotating transmitter is formed by oppositely disposed high frequency antennas 19 respectively mounted on the rotating part 3 and insulated therefrom by insulation 21, and receiving antennas 20 mounted on the stationary part 2 and similarly insulated by insulation 22. Signals from the detector 5, and such other components as may be monitored, are transmitted via the antennas 19 and 20 in contact-free manner for further processing within the stationary part 2, or by external components connected therewith.

Although modifications and changes may be suggested by those skilled in the art it is the intention of the inventor to embody within the patent warranted hereon all changes and modificatons as reasonably and properly come within the scope of his contribution to the art.

I claim as my invention:

1. A computer tomography apparatus comprising:
   a stationary part having a generally circular channel therein;
   a rotatable part mounted for rotation in said channel, said rotatable part having a patient-receiving opening;
   means for generating an x-ray beam and means for detecting the interaction of a patient in said opening with said x-ray beam;
   means for removing heat from at least one of said means for generating an x-ray beam and said means for detecting the interaction of a patient with said x-ray beam;
   a plurality of cooling fins in heat-transferring communication with said means for removing heat and mounted on said rotatable part and projecting into said channnel disposed for movement through said channel as said rotatable part rotates; and
   means for circulating a cooling agent in said channel in contact with said fins as said fins move through said channel.

2. A computer tomography apparatus as claimed in claim 1 wherein said rotatable part has a channel therein in heat-transferring communication with said means for removing heat from said fins, and means for circulating a further cooling agent through said channel.

3. A computer tomography apparatus as claimed in claim 2 wherein said further cooling agent is oil.

4. A computer tomography apparatus as claimed in claim 1 wherein said cooling agent is air.

5. A computer tomography apparatus as claimed in claim 1 wherein said channel has a U-shaped cross-section.

6. A computer tomography apparatus comprising:
   a stationary support having a channel therein;
   a rotatable part mounted for rotation in said channel having a patient-receiving opening therein;
   means on said rotatable part for generating an x-ray beam;
   means on said rotatable part for detecting the interaction of a patient in said opening with said x-ray beam;
   means for circulating cooling agent around at least one of said means for generating said x-ray beam and said means for detecting the interaction of a patient with said x-ray beam for removing heat therefrom, including at least one conduit in said rotatable part through which said cooling agent flows;
   a plurality of cooling fins mounted on said rotatable part in heat-transferring communication with said conduit and projecting into said channel for movement therethrough as said rotatable part rotates; and
   means for circulating another cooling agent in said channel in contact with said fins as said fins move through said channel.

* * * * *